(12) United States Patent
Ober et al.

(10) Patent No.: US 9,527,790 B1
(45) Date of Patent: *Dec. 27, 2016

(54) FLUOROSULFONYL-SUBSTITUTED BIS(ARYL)ACETAL COMPOUNDS

(71) Applicant: DOW Global Technologies LLC, Midland, MI (US)

(72) Inventors: Matthias S. Ober, Midland, MI (US); Patrick Hanley, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,661

(22) Filed: Aug. 18, 2015

(51) Int. Cl.
*C07C 43/225* (2006.01)
*C07F 5/02* (2006.01)

(52) U.S. Cl.
CPC ............ *C07C 43/225* (2013.01); *C07F 5/027* (2013.01)

(58) Field of Classification Search
CPC .... C07C 43/225; C07C 317/14; C07C 317/30; C07F 5/04; C07F 5/05; C07F 5/025; C07F 5/027
See application file for complete search history.

(56) References Cited

U.S. PATENT DOCUMENTS

| 3,733,304 A | 5/1973 | Firth, Jr. |
| 5,204,442 A | 4/1993 | Nye |
| 2015/0025278 A1 | 1/2015 | Ober et al. |

OTHER PUBLICATIONS

Hanley, et al. "Nickel- and Palladium-Catalyzed Coupling of Aryl Fluorosulfonates with Aryl Boronic Acids Enabled by Sulfuryl Fluoride" ACS Catal. Jul. 14, 2015, 5, 5041-5046.
Hanley, et al. "Suzuki Coupling of Aryl Fluorosulfonates Enabled by Sulfuryl Fluoride" OPRD Toronto, Jul. 15, 2015 (32 pages).
Hedayatullah et al., "Sur la synthese de fluorosufates d'aryle", C. R. Acad. Sc. Paris, t. 278, Serie C, pp. 57-59 (Jan. 2, 1974)—with English abstract.
Hopf, et al. From p-Dinnethoxybenzene toward Crown Benzenophanes: 1,3,10,14—Tetraoxa[3.5]paracyclophane, J. Org. Chem. 1992, 57, 5509-5517.
Karakaya, et al. "Full Coverage of a Hydroxy-Substituted Poly(para-phenylene) With First- and Second-Generation Dendritic Wedges Having Isocyanate Focal Points", Acta Polymer, 47, (1996) 79-84.
Liang, et al. "Palladium-Catalyzed, Ligand-Free Suzuki Reaction in Water Using Aryl Fluorosulfates" Org. Lett. Apr. 9, 2015, 17, 1942-1945.
Misuraca, et al. "Relationship Between Conformational Flexibility and Chelate Cooperativity" The Journal of Organic Chemistry, 2011, 76, 2723-2732.
Newman, et al. "Studies on the Monoalkylation of Hydroquinone", J. Org. Chem., vol. 39, No. 2, 1974, pp. 214-215.
Ober et al., U.S. Appl. No. 14/828,628, filed Aug. 18, 2015.
Scheler, et al. "Synthesis and Properties of Alternating Fluorene-Based Oligomers for Sub-um Photopatterning", Macromolecular Chemistry and Physics, 2010, 211, 2081-2089.

*Primary Examiner* — Yate K Cutliff
(74) *Attorney, Agent, or Firm* — Cantor Colburn LLP

(57) ABSTRACT

A bis(aryl)acetal has structure (1)

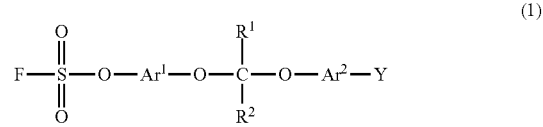

(1)

wherein $Ar^1$ and $Ar^2$ are each independently an aryl or heteroaryl group. $R^1$ and $R^2$ are each independently hydrogen, or an alkyl, cycloalkyl, aryl, or heteroaryl group, and $R^1$ and $R^2$ can connect directly with each other. Y is a leaving group or a boron-containing functional group bonded to $Ar^2$ via a boron atom. The bis(aryl)acetal is useful as a monomer that can be polymerized to yield a polymer with an acid-sensitive backbone.

10 Claims, No Drawings

FLUOROSULFONYL-SUBSTITUTED BIS(ARYL)ACETAL COMPOUNDS

FIELD

The present invention relates to bis(aryl)acetals useful in the synthesis of polyacetals.

INTRODUCTION

Polyacetals are known polymers that have some use in microlithography. (As used herein, for brevity the term "acetal" shall be understood to be generic to "acetal" and "ketal", the term "oligoacetal" shall be understood to be generic to "oligoacetal" and "oligoketal", and the term "polyacetal" shall be understood to be generic to "polyacetal" and "polyketal".) The synthesis of polyacetals typically relies on a polycondensation reaction to form acetal moieties during the polymerization reaction. The reactants include free or protected hydroxyl groups that are consumed in the acetal formation, so the resulting polymers typically do not contain free hydroxyl groups or other functional groups that would interfere with or be consumed in typical acetal formation reactions.

There is a need for materials and methods than can be used to synthesize oligoacetals and polyacetals. It would be desirable if the methods were general to the formation of oligoacetals and polyacetals with and without free hydroxyl groups and other functional groups that are incompatible with polycondensation conditions for formation of oligoacetals and polyacetals.

U.S. Pat. No. 8,933,239 to Ober et al. described bis(aryl) acetal monomers that can be polymerized via Suzuki coupling of aryl groups. The aryl-aryl coupling reaction involves the reaction of a first functional group directly bound to an aryl group and selected from chloro, bromo, iodo, mesylate, tosylate, or triflate with a second functional group that is a boron-containing functional group in which the boron atom is directly bound to an aryl group. While the Ober polymerization method works well, it is known to be sensitive to impurities in the aryl halide. Also, the synthesis and handling of aryl mesylates, tosylates, and triflates adds cost and complexity to the polymerization process.

There is therefore a desire for a simpler polymerization method that does not require a monomer substituted with a chloro, bromo, iodo, mesylate, tosylate, or triflate group.

SUMMARY

One embodiment is a bis(aryl)acetal having structure (1)

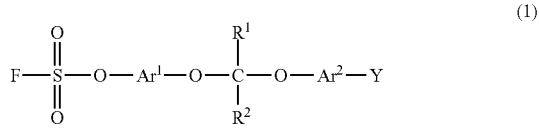

(1)

wherein $Ar^1$ and $Ar^2$ are each independently unsubstituted or substituted $C_{6-18}$ arylene, or unsubstituted or substituted $C_{3-18}$ heteroarylene; $R^1$ and $R^2$ are each independently hydrogen, unsubstituted or substituted $C_{1-12}$ linear or branched alkyl, unsubstituted or substituted $C_{3-20}$ cycloalkyl; unsubstituted or substituted $C_{6-20}$ aryl, or unsubstituted or substituted $C_{3-20}$ heteroaryl; and $R^1$ and $R^2$ are optionally covalently linked to each other to form a ring that includes —$R^1$—C—$R^2$—; and Y is chloro, bromo, iodo, mesylate, tosylate, triflate, fluorosulfonyl (—$OS(O)_2F$), or $B^x$ wherein $B^x$ is a boron-containing functional group bonded to $Ar^2$ via a boron atom.

This and other embodiments are described in detail below.

DETAILED DESCRIPTION

The present inventors have determined that polyaryl polymers can be produced by the catalyzed reaction of an aryl fluorosulfonyl group (—$OS(O)_2F$) with a boron-functionalized aryl group. The two functional group types can reside on the same monomer, which can be polymerized with itself, or on different monomers, which can be copolymerized. The fluorosulfonyl-substituted aryl monomer can be prepared in situ by reaction of the corresponding phenol with sulfuryl fluoride ($FS(O)_2F$), and used without purification other than degassing. The fluorosulfonyl-substituted aryl monomer thus provides a more convenient and less expensive alternative to the chloro-, bromo-, iodo-, mesylate-, tosylate-, and triflate-substituted monomers used in prior art methods.

As used herein, the term "fluorosulfonyl" refers to a —$OS(O)_2F$ group, which is sometimes referred to as a sulfurofluoridate group.

As used herein, "substituted" means including at least one substituent such as a halogen (i.e., F, Cl, Br, I), hydroxyl, amino, thiol, carboxyl, carboxylate, amide, nitrile, sulfide, disulfide, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl. It will be understood that any group or structure disclosed with respect to the formulas herein may be so substituted unless otherwise specified, or where such substitution would significantly adversely affect the desired properties of the resulting structure. Also, "fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

As used herein, "alkyl", whether alone or as part of another group (e.g., in dialkylamino), encompasses straight and branched chain aliphatic groups having the indicated number of carbon atoms. If no number is indicated (e.g., aryl-alkyl-), then 1-6 alkyl carbons are contemplated. Preferred alkyl groups include, without limitation, methyl, ethyl, propyl, isopropyl, butyl, isobutyl, sec-butyl, tert-butyl, pentyl, and hexyl.

As used herein, "cycloalkyl", whether alone as part of another group, encompasses fully saturated aliphatic cyclic groups having the indicated number of carbon atoms. In no number of carbon atoms is indicated, then 3 to 12 atoms are contemplated. Preferred cycloalkyl groups include cyclopropyl, cyclobutyl, cyclopropyl, 1-methylcyclopropyl, cyclohexyl, cyclooctyl, cyclodecyl, and cyclododecyl.

As used herein, "aryl" is an aromatic moiety comprising one to three aromatic rings. In one instance, the aryl group is a $C_{6-18}$ aryl group. In some embodiments, the aryl group is a $C_{6-10}$ aryl group. In some embodiments, the aryl group is a $C_{10-18}$ aryl group. Aryl groups contain 4n+2 pi electrons, where n is an integer. Preferred aryls include, without limitation, phenyl, biphenyl, naphthyl, anthracenyl, phenanthrenyl, pyrenyl, and fluorenyl. Unless otherwise indicated, the aryl group is optionally substituted with 1 or more substituents that are compatible with the syntheses described herein. Such substituents include, but are not limited to, sulfonate groups, boron-containing groups, $C_{1-6}$ alkyl, nitro, halogen, cyano, carboxylic acids (e.g., $C_{0-6}$—COOH), esters, amides, and $C_2$-$C_6$ alkenyl. Other substituents are known in the art. Unless otherwise indicated, the foregoing substituent groups are not themselves further substituted.

As used herein, "heteroaryl" refers to an aromatic ring system containing at least one heteroatom selected from nitrogen, oxygen, and sulfur. Preferably, the heteroaryl group is a five or six-membered ring. The heteroaryl ring may be fused or otherwise attached to one or more heteroaryl rings, aromatic or non-aromatic hydrocarbon rings or heterocycloalkyl rings. Examples of heteroaryl groups include, without limitation, pyridine, pyrimidine, pyridazine, pyrazine and furan. The heteroaryl group may be optionally substituted with 1 or more substituents that are compatible with the syntheses described herein. Such substituents include, but are not limited to, fluorosulfonate groups, boron-containing groups, $C_{1-6}$ alkyl, nitro, halogen, cyano, carboxylic acids (e.g., $C_{0-6}$—COOH), esters, amides and $C_{2-6}$ alkene. Other substituents are known in the art. Unless otherwise indicated, the foregoing substituent groups are not themselves further substituted.

One embodiment is a bis(aryl)acetal having structure (1)

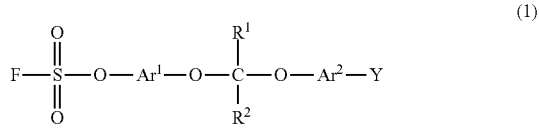

(1)

wherein $Ar^1$ and $Ar^2$ are each independently unsubstituted or substituted $C_{6-18}$ arylene, or unsubstituted or substituted $C_{3-18}$ heteroarylene; $R^1$ and $R^2$ are each independently hydrogen, unsubstituted or substituted $C_{1-12}$ linear or branched alkyl, unsubstituted or substituted $C_{3-20}$ cycloalkyl; unsubstituted or substituted $C_{6-20}$ aryl, or unsubstituted or substituted $C_{3-20}$ heteroaryl; and $R^1$ and $R^2$ are optionally covalently linked to each other to form a ring that includes —$R^1$—C—$R^2$—; and Y is chloro, bromo, iodo, mesylate, tosylate, triflate, fluorosulfonyl (—$OS(O)_2F$), or $B^x$ wherein $B^x$ is a boron-containing functional group bonded to $Ar^2$ via a boron atom.

In structure (1), $Ar^1$ and $Ar^2$ are each independently unsubstituted or substituted $C_{6-18}$ arylene, or unsubstituted or substituted $C_{3-18}$ heteroarylene. In some embodiments, at least one of $Ar^1$ and $Ar^2$ is substituted with at least one functional group selected from the group consisting of hydroxyl, acetals, ketals, esters, and lactones.

Examples of $Ar^1$ and $Ar^2$ include

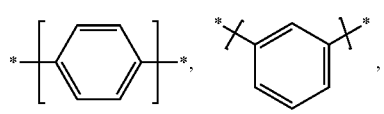

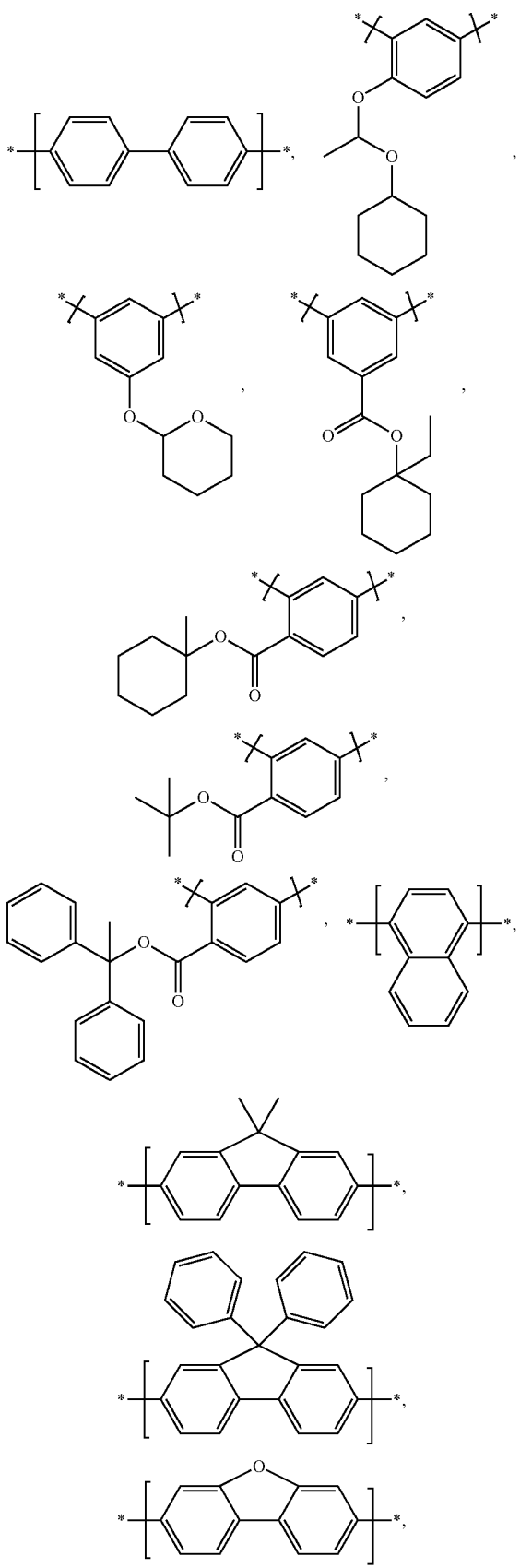

-continued

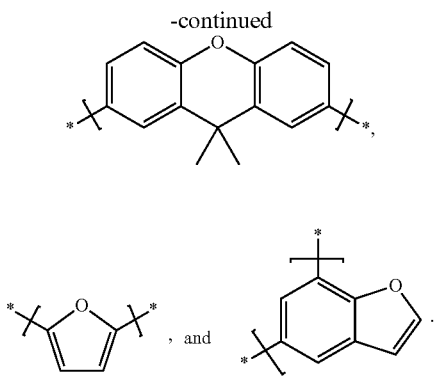

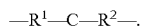, and

In some embodiments, $Ar^1$ and $Ar^2$ are each independently 1,3-phenylene, 1,4-phenylene, or 4,4'-biphenylene.

In structure (1), $R^1$ and $R^2$ are each independently hydrogen, unsubstituted or substituted $C_{1-12}$ linear or branched alkyl, unsubstituted or substituted $C_{3-20}$ cycloalkyl; unsubstituted or substituted $C_{6-20}$ aryl, or unsubstituted or substituted $C_{3-20}$ heteroaryl; and $R^1$ and $R^2$ are optionally covalently linked to each other to form a ring that includes

—$R^1$—C—$R^2$—.

Specific examples of $R^1$ and $R^2$ include hydrogen, methyl, hydroxymethyl, adamant-1-yl, adamant-2-yl, furan-2-yl, phenyl, 3-bromophenyl, 4-t-butylphenyl, 2-methoxyphenyl, 3-methoxyphenyl, 4-methoxyphenyl, 4-(fluorosulfonyl)phenyl, 2,4,6-trimethoxyphenyl, 4-ethoxyphenyl, 4-(2-propoxy)phenyl, 2-hydroxyphenyl, 3-hydroxyphenyl, 4-hydroxyphenyl, benzofuran-2-yl, benzofuran-5-yl, isobenzofuran-4-yl, isobenzofuran-5-yl, xanthen-4-yl, 9,9-dimethylxanthen-4-yl, xanthen-9-yl, 1,1'-biphen-2-yl, 2'-methoxy-1,1'-biphen-2-yl, 1,1'-biphen-3-yl, 3'-methoxy-1,1'-biphen-3-yl, 1,1'-biphen-4-yl, naphth-1-yl, 2-methoxynaphth-1-yl, 4-methoxynaphth-1-yl, naphth-2-yl, 6-methoxynaphth-2-yl, 1-fluorenyl, 2-fluorenyl, 9,9-dimethyl-2-fluorenyl, anthracen-2-yl, anthracen-9-yl, phenanthren-2-yl, phenanthren-9-yl, or pyren-2-yl; or $R^1$ and $R^2$ are covalently linked to each other to form

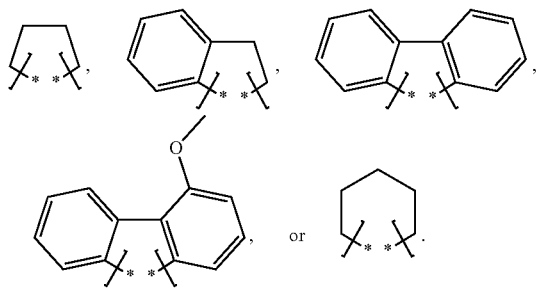

In structure (1), Y is chloro, bromo, iodo, mesylate, tosylate, triflate, fluorosulfonyl (—OS(O)$_2$F), or $B^x$ wherein $B^x$ is a boron-containing functional group bonded to $Ar^2$ via a boron atom. In some embodiments, Y is $B^x$, and $B^x$ is selected from the group consisting of —BF$_3^-$M$^+$, wherein each occurrence of M$^+$ is independently an alkali metal cation, or an unsubstituted or substituted ammonium ion; —B(OH)$_2$;

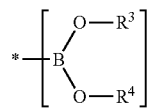

wherein $R^3$ and $R^4$ are each independently $C_{1-18}$ alkyl, $C_{3-18}$ cycloalkyl, or $C_{6-18}$ aryl; and $R^3$ and $R^4$ are optionally covalently linked to each other to form a ring that includes

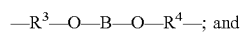; and

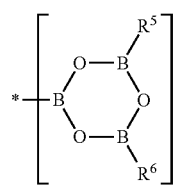

wherein $R^5$ and $R^6$ are each independently hydrogen, unsubstituted or substituted $C_{1-12}$ linear or branched alkyl, unsubstituted or substituted $C_{3-12}$ cycloalkyl, unsubstituted or substituted $C_{6-12}$ aryl, unsubstituted or substituted $C_{3-12}$ heteroaryl, or

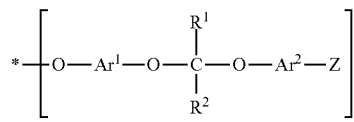

wherein $Ar^1$, $Ar^2$, $R^1$, and $R^2$ are defined as for structure (1); and wherein Z is chloro, bromo, iodo, mesylate, tosylate, triflate, fluorosulfonyl (—OS(O)$_2$F), or $B^z$ wherein $B^z$ is selected from the group consisting of —BF$_3^-$M$^+$, wherein each occurrence of M$^+$ is independently an alkali metal cation, or an unsubstituted or substituted ammonium ion; —B(OH)$_2$; and

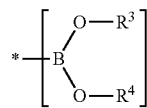

wherein $R^3$ and $R^4$ are each independently $C_{1-18}$ alkyl, $C_{3-18}$ cycloalkyl, or $C_{6-18}$ aryl; and $R^3$ and $R^4$ are optionally covalently linked to each other to form a ring that includes

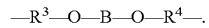.

In some embodiments, Y is $B^x$, and $B^x$ is

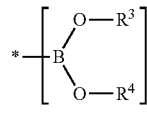

wherein $R^3$ and $R^4$ are each independently $C_{1-18}$ alkyl, $C_{3-18}$ cycloalkyl, or $C_{6-18}$ aryl; and $R^3$ and $R^4$ are optionally covalently linked to each other to form a ring that includes

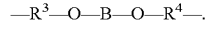.

In some embodiments of structure (1), Y is fluorosulfonyl (—OS(O)$_2$F).
Specific examples of compounds according to structure (1) and containing at least one fluorosulfonyl group and at least one boron-containing functional group include
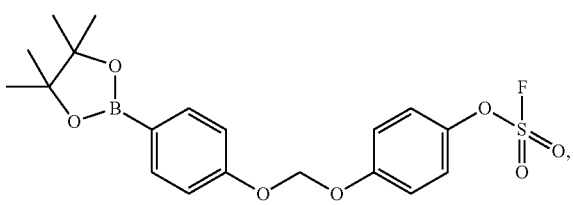
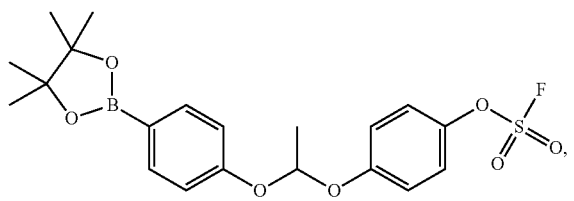
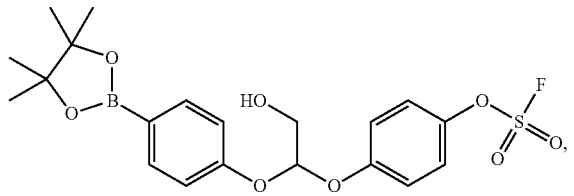
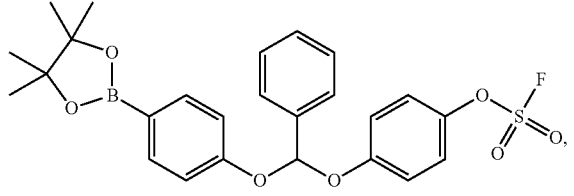
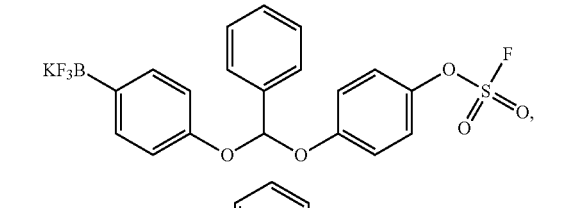
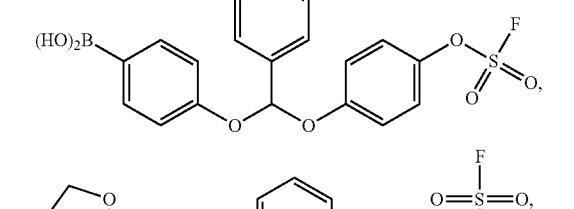
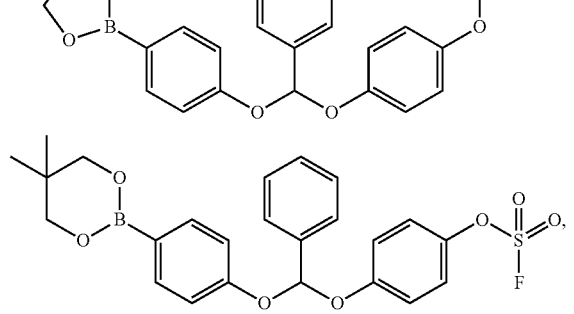
-continued
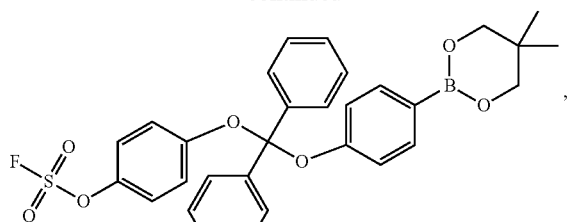
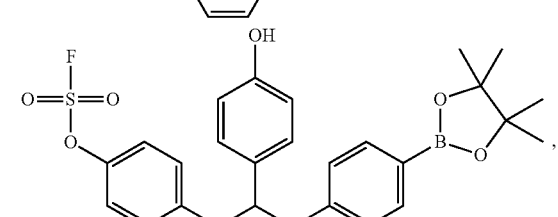
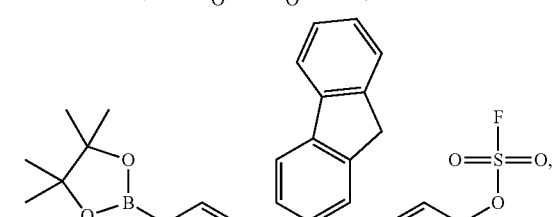
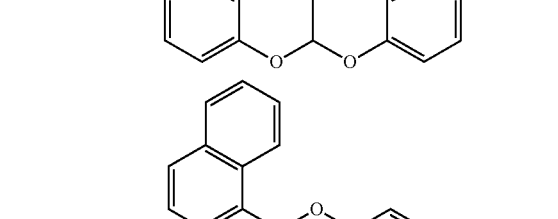
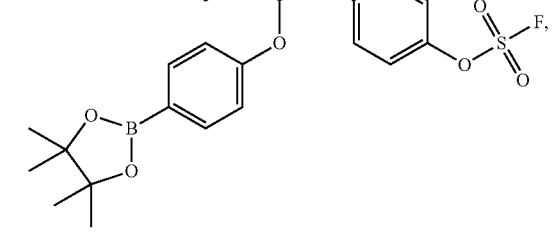
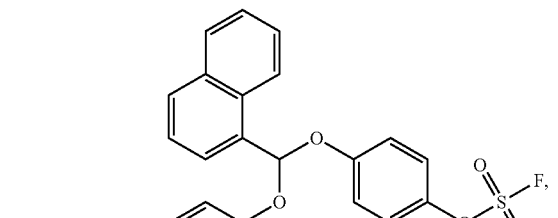
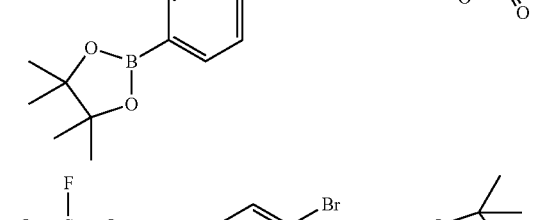
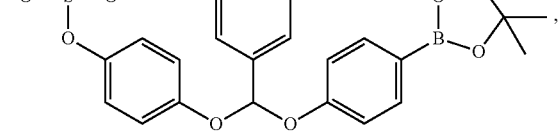

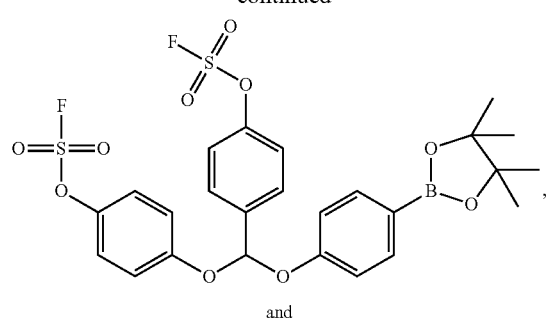
and
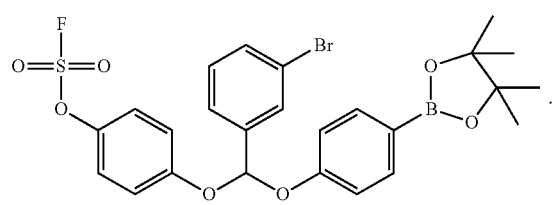
Specific examples of compounds according to structure (1) and containing at least two fluorosulfonyl groups include
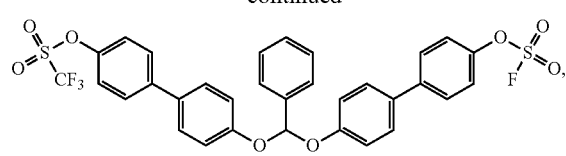
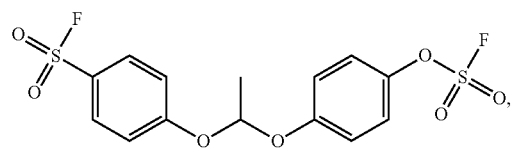
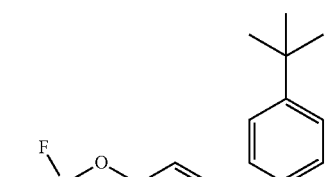
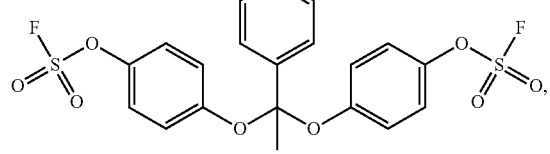
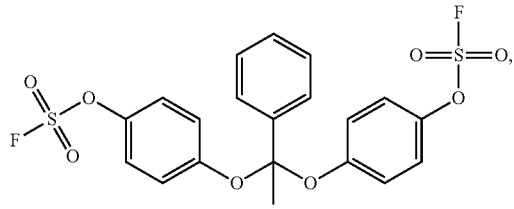
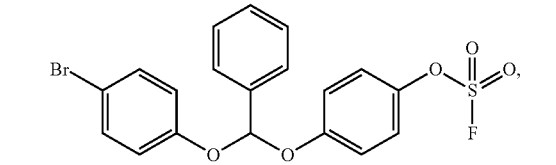
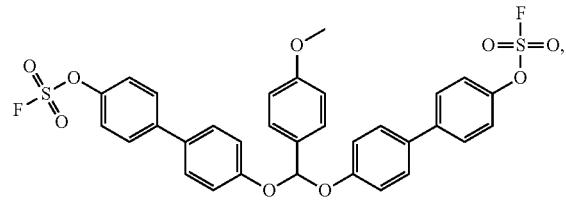
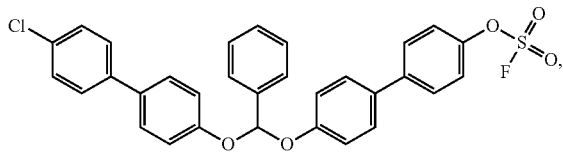
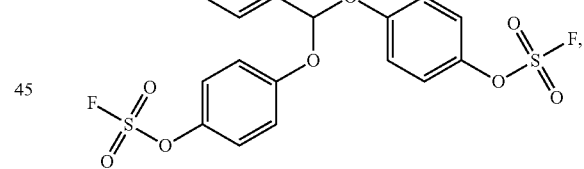
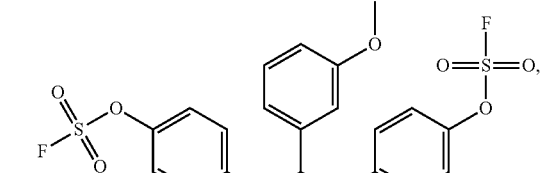
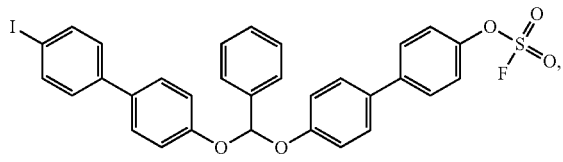
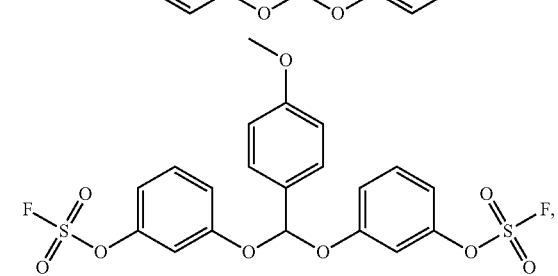

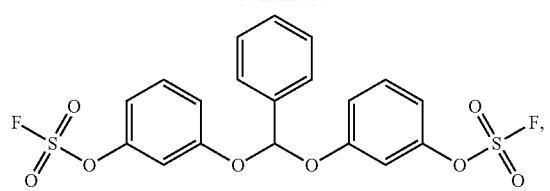
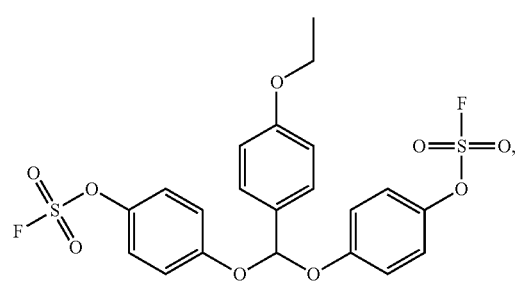
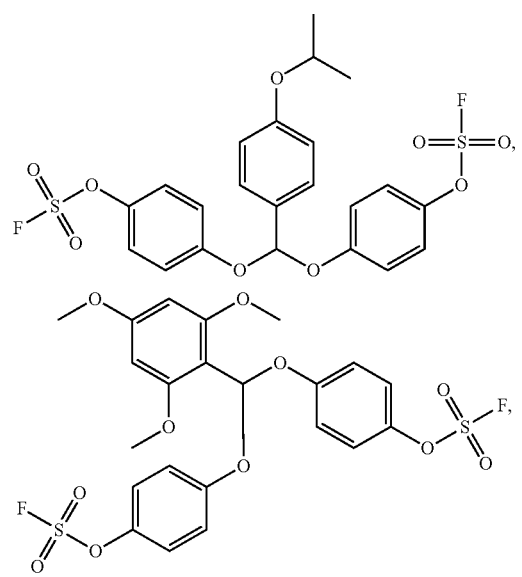
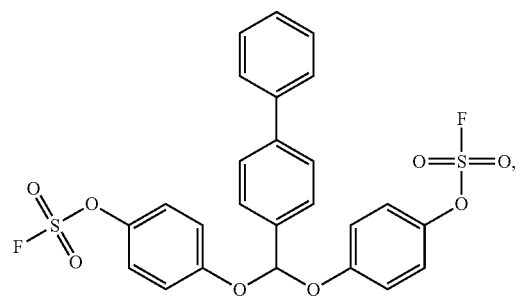
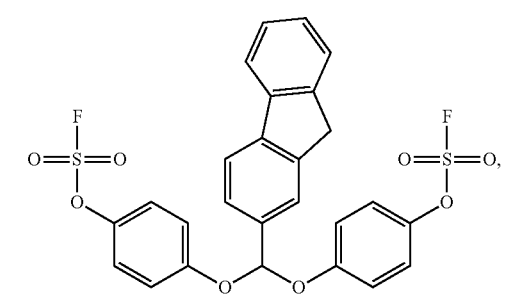
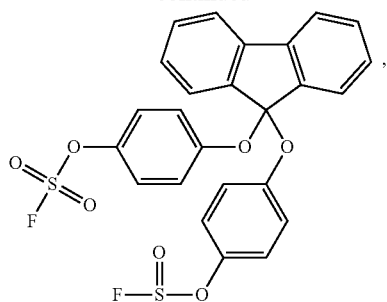
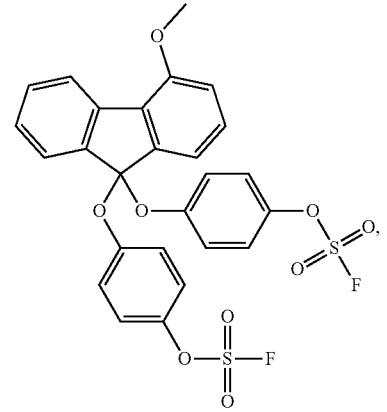
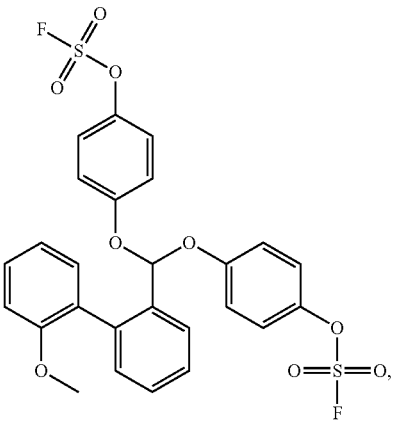
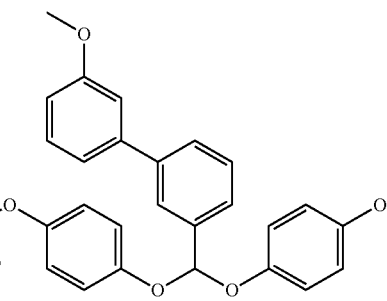
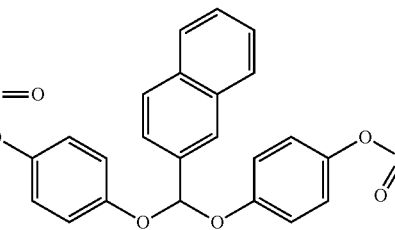

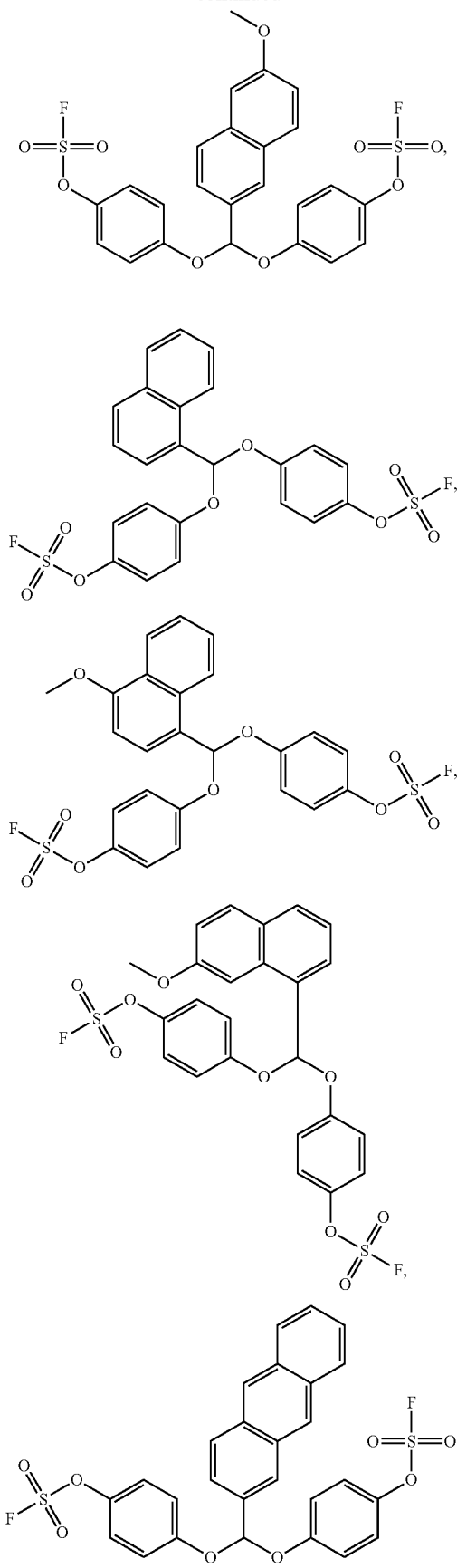

15
-continued
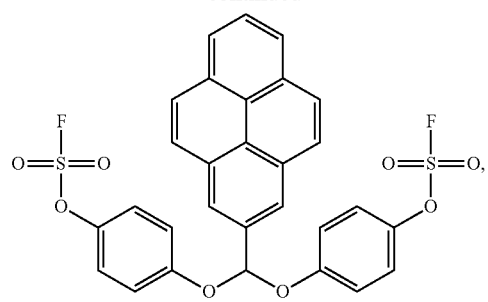
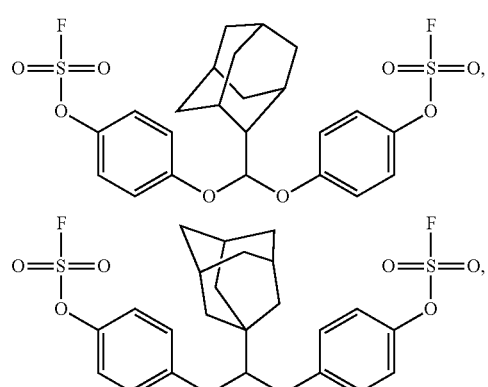
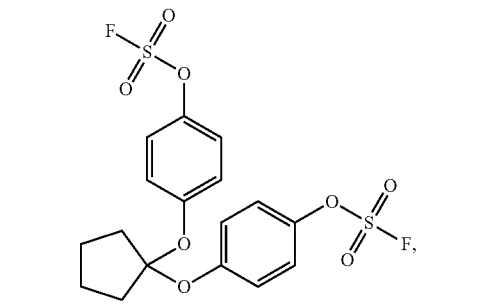
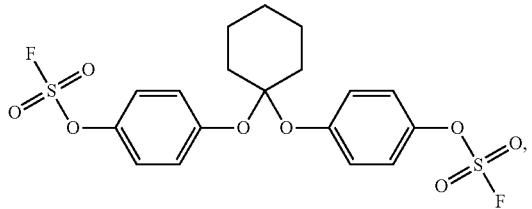
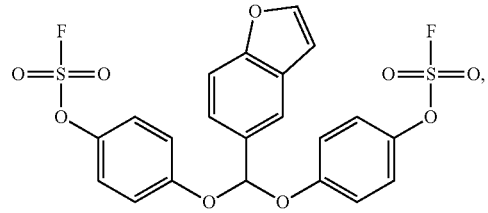
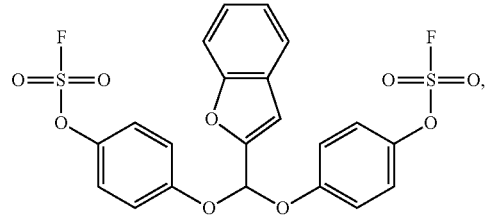
16
-continued
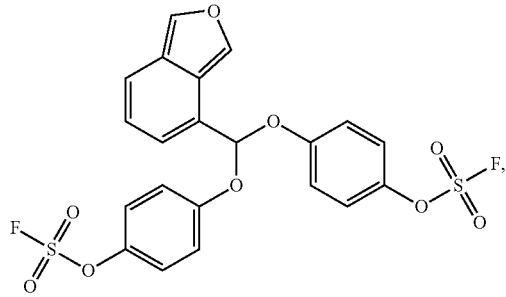
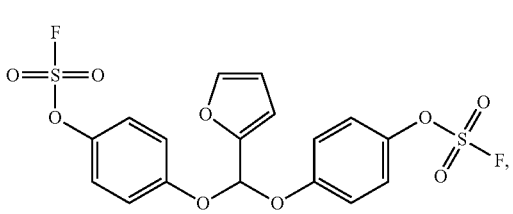
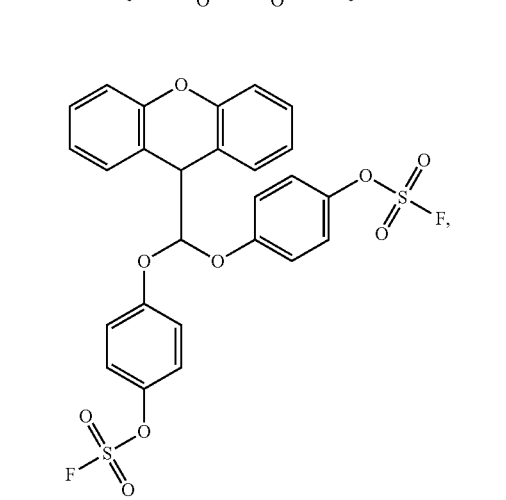
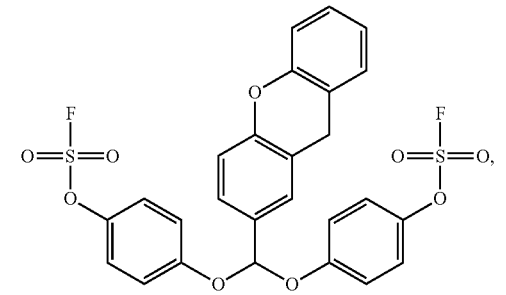
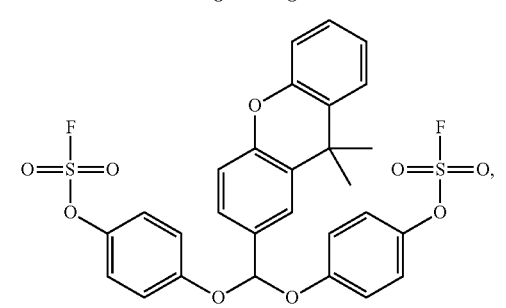

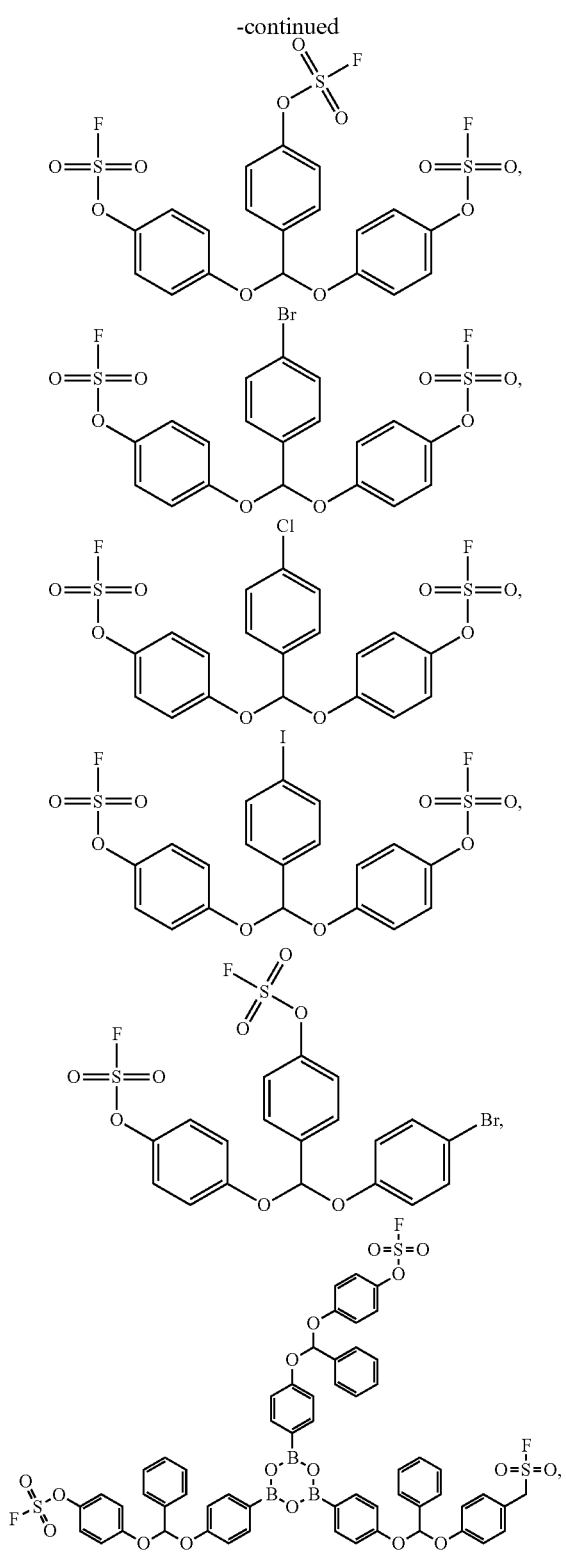

and combinations thereof.

The compounds are useful as monomers for forming poly(aryl) polymers. When the compound according to structure (1) includes a fluorosulfonate group and a boron-containing functional group, it can be homopolymerized in the presence of a base and a catalyst comprising a group 10 atom (i.e., Ni, Pd, or Pt). When the compound according to structure (1) includes two or more fluorosulfonate groups and no boron-containing functional group, it can be copolymerized with an aryl monomer comprising at least two boron-containing functional groups. Details of the polymerization method can be found in co-filed U.S. patent application Ser. No. 14/828,628.

EXAMPLES 4,4'-(Methylenebis(oxy))diphenol 4,4'-(methylenebis(oxy))diphenol, shown below,

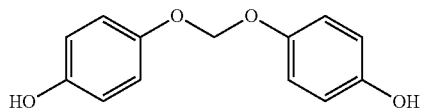 [SMILES: Oc1ccc(OCOc2ccc(O)cc2)cc1]

can be synthesized according to H. Hopf et al., *J. Org. Chem.*, 1992, 57, 5509-5517 (compound 3a); or Misuraca et al. *J. Org. Chem.* 2011, 76, 2723-2732 (Compound 3b).

4,4'-((Phenylmethylene)bis(oxy))diphenol

With reference to Newman et al. *J. Org. Chem.* 1974, 39, 214-215, 4,4'-((Phenylmethylene)bis(oxy))diphenol, shown below,

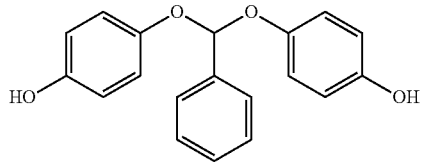 [SMILES: Oc1ccc(OC(Oc2ccc(O)cc2)c2ccccc2)cc1]

is synthesized by the following prophetic procedure. Inside a glove box 4,4'-((phenylmethylene)bis(oxy))diphenol is accessed by reacting hydroquinone (5.5 grams, 50 millimoles, 2.5 equivalents) in DMSO (40 mL) with sodium hydride (98%, 2.45 grams, 100 millimoles, 5 equivalents) to receive the disodium salt. The reaction is heated to 70° C. and α,α-dichlorotoluene (2.98 milliliters, 20 millimoles, 1.0 equivalent) in DMSO (10 mL) is added over the course of several hours via syringe pump. The reaction is stirred overnight and then quenched by addition to water (200 milliliters). The aqueous phase is extracted with a 1:1 mixture of diethyl ether and ethyl acetate (3×120 milliliters). The combined organic phases are then washed with deionized water (5×100 milliliters), brine (1×100 milliliters) and dried over magnesium sulfate. After filtration and concentration on the rotary evaporator, the residue is taken up in diethyl ether (60 milliliters) and filtered through a plug of basic alumina. The product is fully eluted with additional diethyl ether (700 milliliters) and concentrated on a rotary evaporator.

(Methylenebis(oxy))bis(4,1-phenylene) bis(sulfurofluoridate)

(Methylenebis(oxy))bis(4,1-phenylene) bis(sulfurofluoridate), shown below,

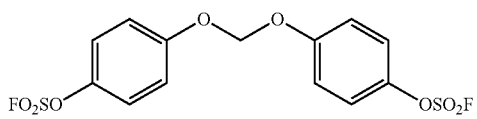

is synthesized by the following prophetic procedure. To a 30 milliliter vial is added the starting material 4,4'-(methylenebis(oxy))diphenol (290 milligrams; 1.25 millimoles). Potassium carbonate (1.20 gram; 8.75 millimoles, 7 equivalents) is added. A saturated solution of sulfuryl fluoride in 1,4-dioxane (13.5 milliliters) is added via syringe and the vial is tightly capped. (Alternatively, sulfuryl fluoride is bubbled through a solution of the starting material and dioxane with potassium carbonate. Alternatively, a reactor is charged with the starting material, 1,4-dioxane and potassium carbonate and the reactor is pressurized with sulfuryl fluoride.) The progress of each reaction is checked by gas chromatography/mass spectroscopy analysis. When greater than 95% conversion to (methylenebis(oxy))bis(4,1-phenylene) bis(sulfurofluoridate) is observed, that product is isolated by filtration to remove solids, followed by concentration of the filtrate under reduced pressure.

(Phenylmethylene)bis(oxy))bis(4,1-phenylene) bis(sulfurofluoridate ((Phenylmethylene)bis(oxy))bis(4,1-phenylene) bis(sulfurofluoridate), shown below,

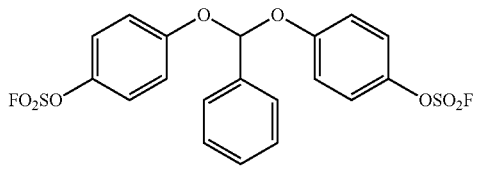

is synthesized by the following prophetic procedure. To a 30 milliliter vial is added 4,4'-((phenylmethylene)bis(oxy))diphenol (385 milligrams; 1.25 millimoles). Potassium carbonate (1.20 grams; 8.75 millimoles, 7 equivalents) is added. A saturated solution of sulfuryl fluoride in 1,4-dioxane (13.5 milliliters) is added via syringe and the vial is tightly capped. (Alternatively, sulfuryl fluoride is bubbled through a solution of the starting material and dioxane with potassium carbonate. Alternatively, a reactor is charged with the starting material, 1,4-dioxane and potassium carbonate and the reactor is pressurized with sulfuryl fluoride.) The progress of each reaction is checked by gas chromatography/mass spectroscopy analysis. When greater than 95% conversion to ((phenylmethylene)bis(oxy))bis(4,1-phenylene) bis(sulfurofluoridate) is observed, it is isolated by filtration to remove solids, followed by concentration of the filtrate under reduced pressure.

4-((4-(4,4,5,5-Tetramethyl-1,3,2-dioxaborolan-2-yl)phenoxy)methoxy)phenyl sulfurofluoridate 4-((4-(4,4,5,5-Tetramethyl-1,3,2-dioxaborolan-2-yl)phenoxy)methoxy)phenyl sulfurofluoridate, shown below,

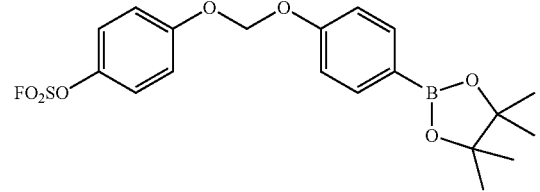

is synthesized by the following prophetic procedure. Inside a nitrogen-purged glovebox, to a 30 milliliter vial is added (methylenebis(oxy))bis(4,1-phenylene) bis(sulfurofluoridate) (396 milligrams, 1 millimole, 1 equivalent) and 1,4-dioxane (5 milliliters). Potassium acetate (294 milligrams, 3 millimoles, 3 equivalents) is added along with bis(pinacolato)diboron (267 milligrams, 1.05 millimoles, 1.05 equivalents) and catalyst [1,1'-bis(diphenylphosphino)ferrocene]dichloro-palladium(II), complex with dichloromethane (8.2 milligrams, 10 micromoles, 0.01 equivalents). The reaction is heated to 80° C. and stirred overnight. Depending on the content of trace water, homopolymerization might be observed as a side reaction, which, in some embodiments, may be the desired subsequent reaction. The title compound is isolated by extracting with ethyl acetate, followed by filtration through a short plug of alumina and removal of solvent under reduced pressure.

4-(Phenyl(4-(4,4,5,5-tetramethyl-1,3,2-dioxaborolan-2-yl)phenoxy)methoxy)phenyl sulfurofluoridate 4-(Phenyl(4-(4,4,5,5-tetramethyl-1,3,2-dioxaborolan-2-yl)phenoxy)methoxy)phenyl sulfurofluoridate, shown below,

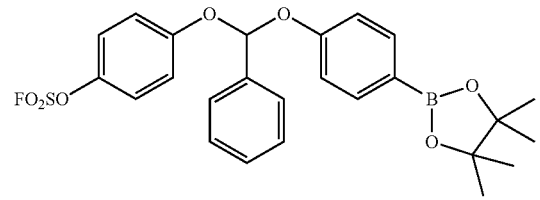

is synthesized by the following prophetic procedure. Inside a nitrogen-purged glovebox, to a 30 milliliter vial is added ((phenylmethylene)bis(oxy))bis(4,1-phenylene) bis(sulfurofluoridate) (472 milligrams, 1 millimole, 1 equivalent) and 1,4-dioxane (5 milliliters). Potassium acetate (294 milligrams, 3 millimoles, 3 equivalents) is added along with bis(pinacolato)diboron (267 milligrams, 1.05 millimoles, 1.05 equivalents) and catalyst [1,1'-bis(diphenylphosphino)ferrocene]dichloro-palladium(II), complex with dichloromethane (8.2 milligrams, 10 micromoles, 0.01 equivalents). The reaction mixture is heated to 80° C. and stirred overnight. Depending on the content of trace water, homopolymerization might be observed as a side reaction, which, in some embodiments, may be the desired subsequent reaction. The title compound is isolated by extracting with ethyl acetate, followed by filtration through a short plug of alumina and removal of solvent under reduced pressure.

The invention claimed is:

1. A bis(aryl)acetal having structure (1)

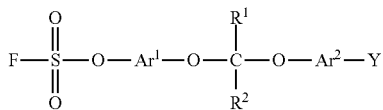

wherein
Ar$^1$ and Ar$^2$ are each independently unsubstituted or substituted C$_{6-18}$ arylene, or unsubstituted or substituted C$_{3-18}$ heteroarylene;
R$^1$ and R$^2$ are each independently hydrogen, unsubstituted or substituted C$_{1-12}$ linear or branched alkyl, unsubstituted or substituted C$_{3-20}$ cycloalkyl; unsubstituted or substituted C$_{6-20}$ aryl, or unsubstituted or substituted C$_{3-20}$ heteroaryl; and R$^1$ and R$^2$ are optionally covalently linked to each other to form a ring that includes
—R$^1$—C—R$^2$—; and
Y is chloro, bromo, iodo, mesylate, tosylate, triflate, fluorosulfonyl (—OS(O)$_2$F), or B$^x$ wherein B$^x$ is a boron-containing functional group bonded to Ar$^2$ via a boron atom.

2. The bis(aryl)acetal of claim 1, wherein Y is B$^x$, and B$^x$ is selected from the group consisting of —BF$_3$$^-$M$^+$, wherein each occurrence of M$^+$ is independently an alkali metal cation, or an unsubstituted or substituted ammonium ion; —B(OH)$_2$;

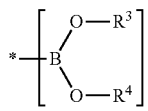

wherein R$^3$ and R$^4$ are each independently C$_{1-18}$ alkyl, C$_{3-18}$ cycloalkyl, or C$_{6-18}$ aryl; and R$^3$ and R$^4$ are optionally covalently linked to each other to form a ring that includes
—R$^3$—O—B—O—R$^4$—; and

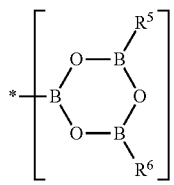

wherein R$^5$ and R$^6$ are each independently hydrogen, unsubstituted or substituted C$_{1-12}$ linear or branched alkyl, unsubstituted or substituted C$_{3-12}$ cycloalkyl, unsubstituted or substituted C$_{6-12}$ aryl, unsubstituted or substituted C$_{3-12}$ heteroaryl, or

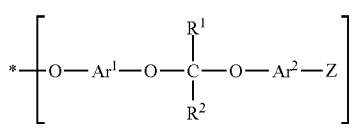

wherein Ar$^1$, Ar$^2$, R$^1$, and R$^2$ are defined as in claim 1; and
wherein Z is chloro, bromo, iodo, mesylate, tosylate, triflate, fluorosulfonyl (—OS(O)$_2$F), or B$^z$ wherein B$^z$ is selected from the group consisting of —BF$_3$$^-$M$^+$, wherein each occurrence of M$^+$ is independently an alkali metal cation, or an unsubstituted or substituted ammonium ion; —B(OH)$_2$; and

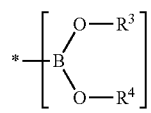

wherein R$^3$ and R$^4$ are each independently C$_{1-18}$ alkyl, C$_{3-18}$ cycloalkyl, or C$_{6-18}$ aryl; and R$^3$ and R$^4$ are optionally covalently linked to each other to form a ring that includes
—R$^3$—O—B—O—R$^4$—.

3. The bis(aryl)acetal of claim 1, wherein B$^x$ is

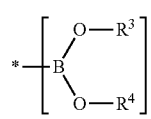

wherein R$^3$ and R$^4$ are each independently C$_{1-18}$ alkyl, C$_{3-18}$ cycloalkyl, or C$_{6-18}$ aryl; and R$^3$ and R$^4$ are optionally covalently linked to each other to form a ring that includes
—R$^3$—O—B—O—R$^4$—.

4. The bis(aryl)acetal of claim 1, wherein Y is fluorosulfonyl.

5. The bis(aryl)acetal of claim 1, wherein at least one of Ar$^1$ and Ar$^2$ is substituted with at least one functional group selected from the group consisting of hydroxyl, acetals, ketals, esters, and lactones.

6. The bis(aryl)acetal of claim 1, wherein Ar$^1$ and Ar$^2$ are each independently selected from the group consisting of

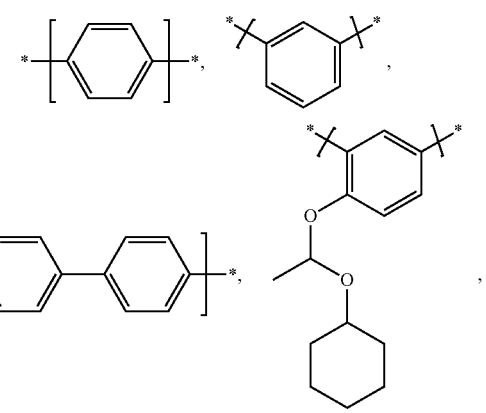

-continued

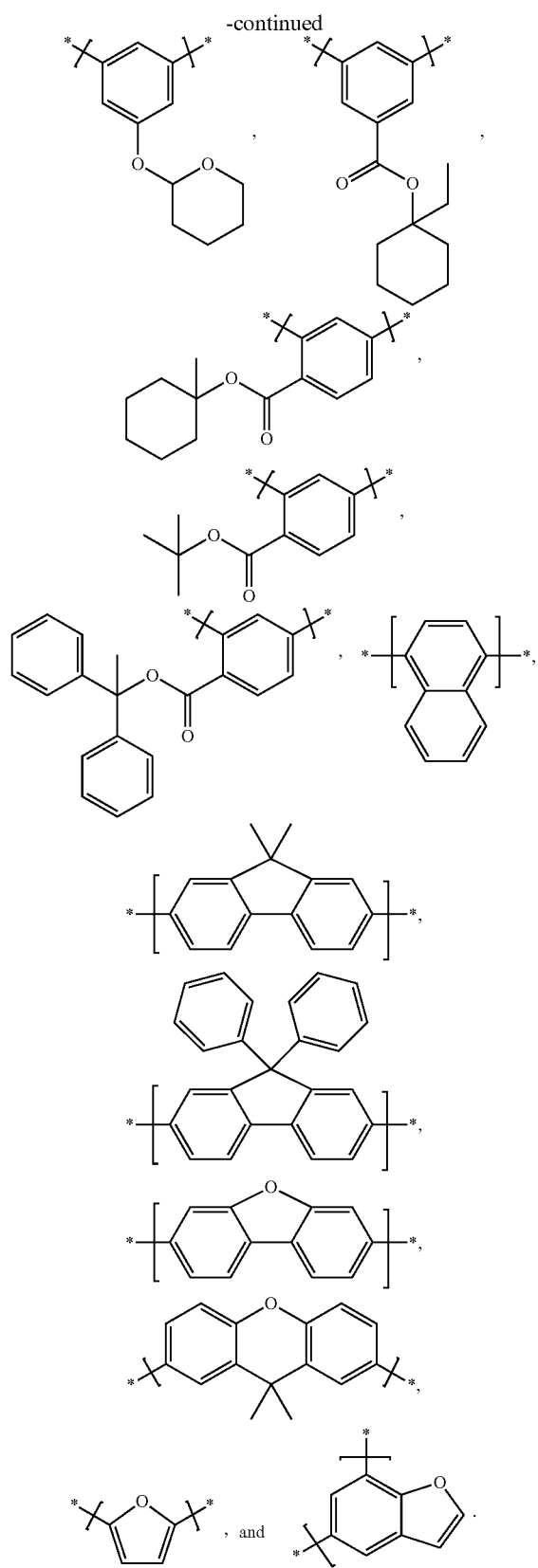

7. The bis(aryl)acetal of claim 1, wherein Ar¹ and Ar² are each independently 1,3-phenylene, 1,4-phenylene, or 4,4'-biphenylene.

8. The bis(aryl)acetal of claim 1, wherein $R^1$ and $R^2$ are each independently hydrogen, methyl, hydroxymethyl, adamant-1-yl, adamant-2-yl, furan-2-yl, phenyl, 3-bromophenyl, 4-t-butylphenyl, 2-methoxyphenyl, 3-methoxyphenyl, 4-methoxyphenyl, 4-(fluoro sulfonyl)phenyl, 2,4,6-trimethoxyphenyl, 4-ethoxyphenyl, 4-(2-propoxy)phenyl, 2-hydroxyphenyl, 3-hydroxyphenyl, 4-hydroxyphenyl, benzofuran-2-yl, benzofuran-5-yl, isobenzofuran-4-yl, isobenzofuran-5-yl, xanthen-4-yl, 9,9-dimethylxanthen-4-yl, xanthen-9-yl, 1,1'-biphen-2-yl, 2'-methoxy-1,1'-biphen-2-yl, 1,1'-biphen-3-yl, 3'-methoxy-1,1'-biphen-3-yl, 1,1'-biphen-4-yl, naphth-1-yl, 2-methoxynaphth-1-yl, 4-methoxynaphth-1-yl, naphth-2-yl, 6-methoxynaphth-2-yl, 1-fluorenyl, 2-fluorenyl, 9,9-dimethyl-2-fluorenyl, anthracen-2-yl, anthracen-9-yl, phenanthren-2-yl, phenanthren-9-yl, or pyren-2-yl; or $R^1$ and $R^2$ are covalently linked to each other to form

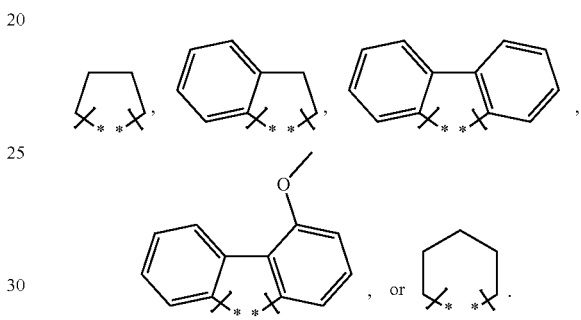

9. The bis(aryl)acetal of claim 1, selected from the group consisting of

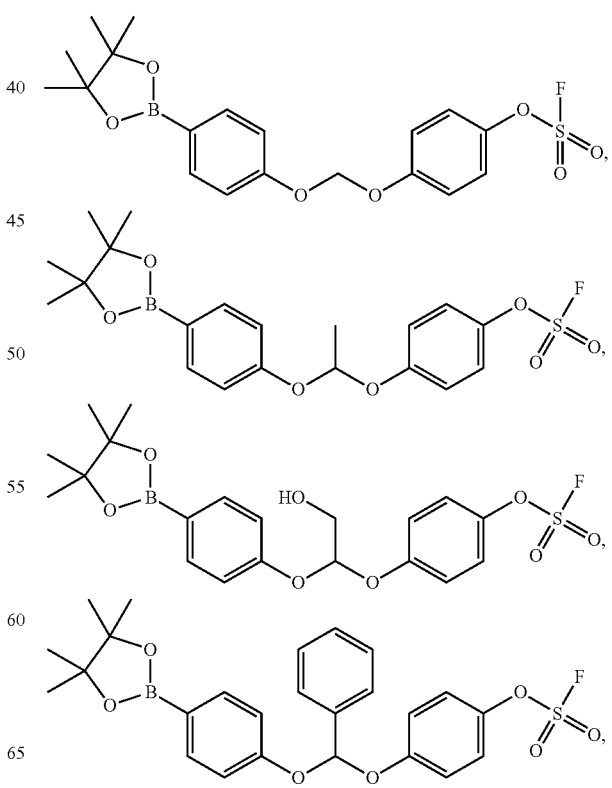

-continued
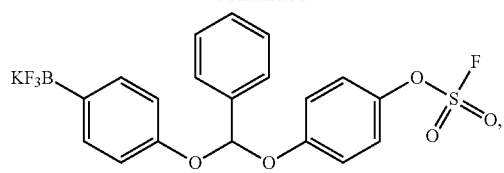
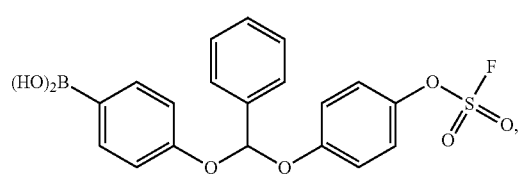
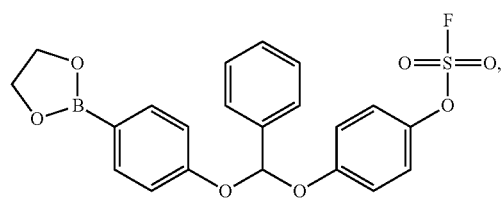
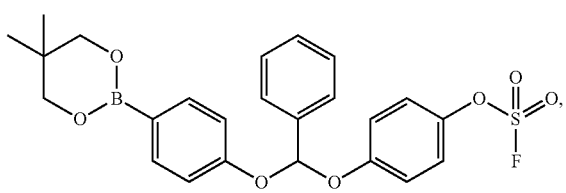
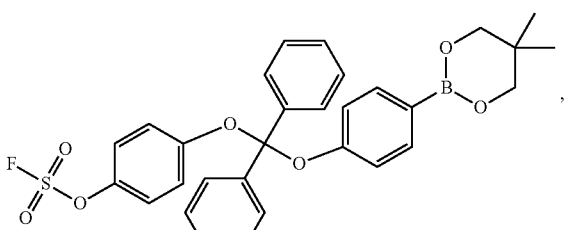
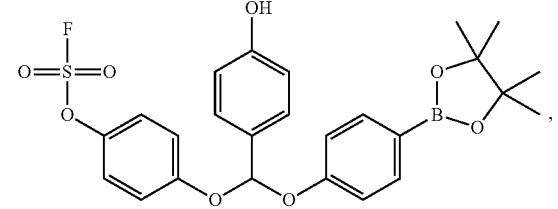
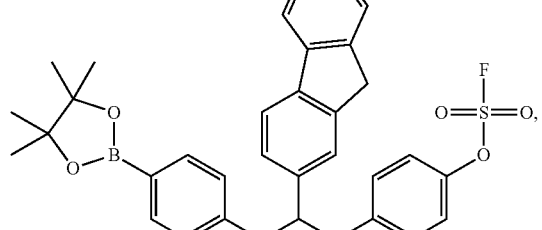
-continued
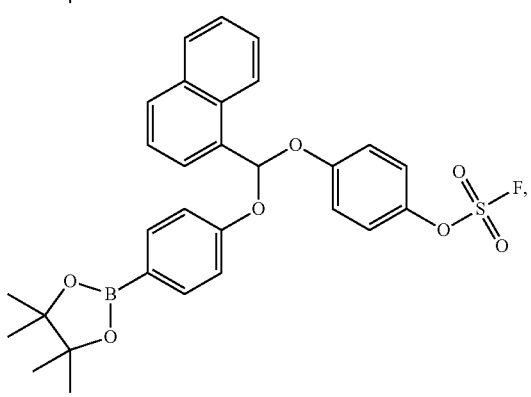
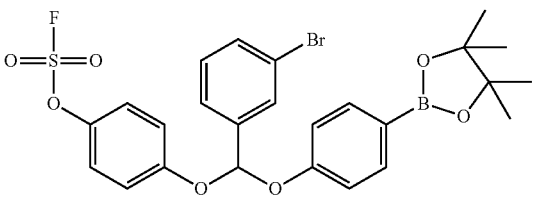
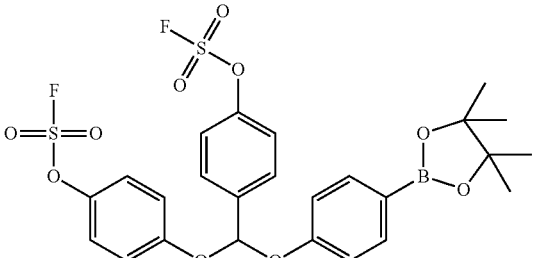
and
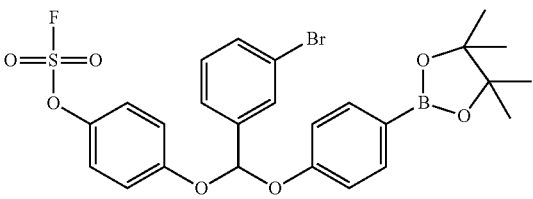
10. The bis(aryl)acetal of claim 1, selected from the group consisting of 27                                28
                              -continued 29
-continued
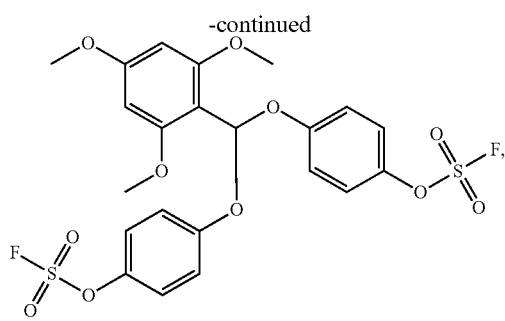
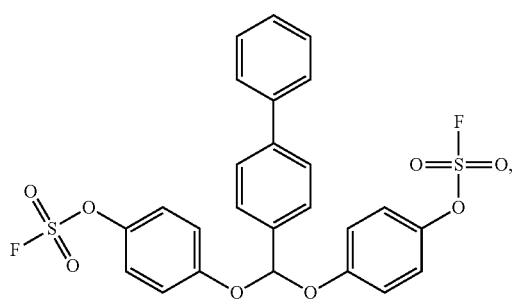
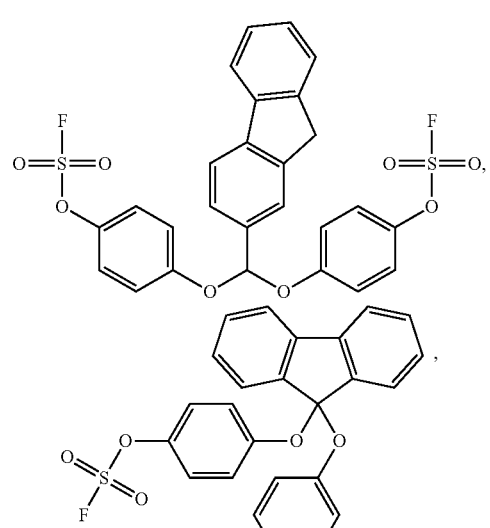
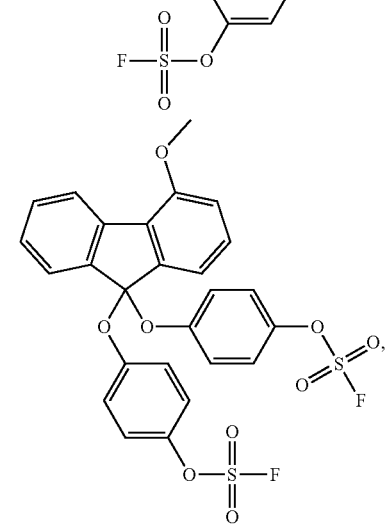
30
-continued
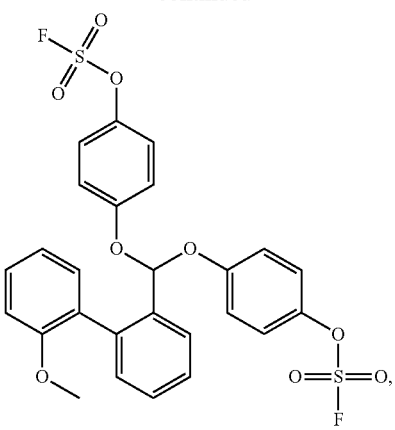
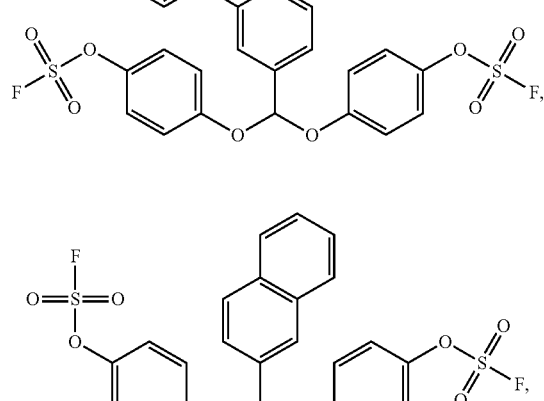
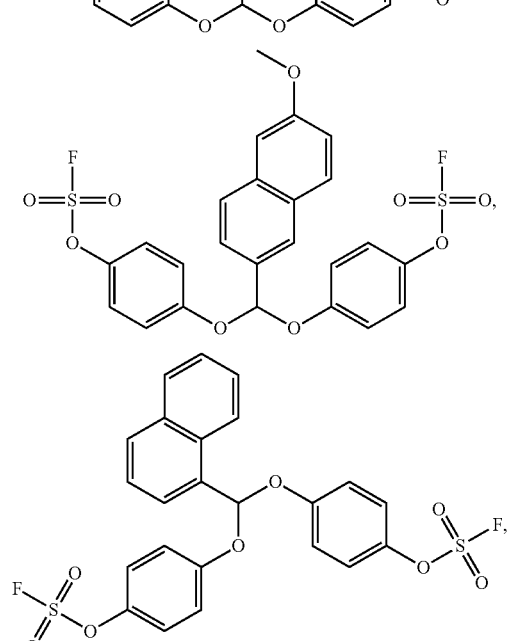

-continued
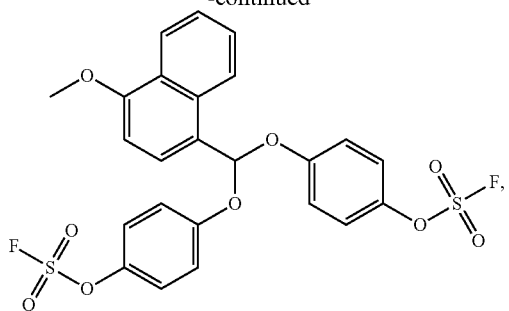
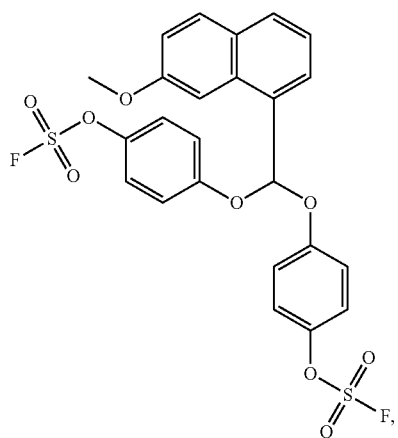 [SMILES: COc1ccc2cccc(C(Oc3ccc(OS(=O)(=O)F)cc3)Oc3ccc(OS(=O)(=O)F)cc3)c2c1]
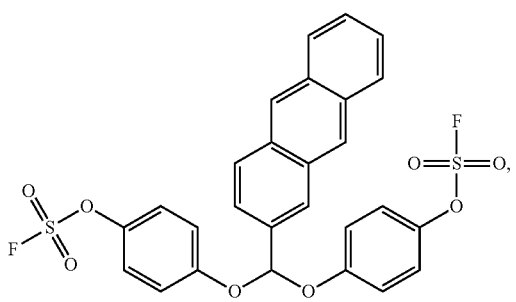
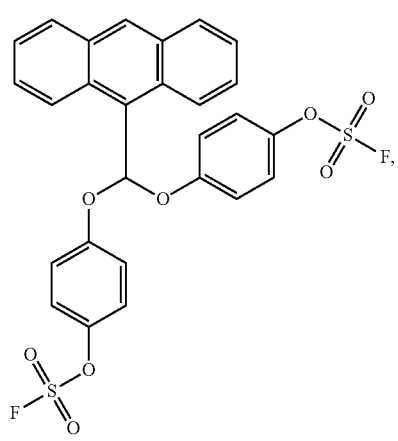
-continued
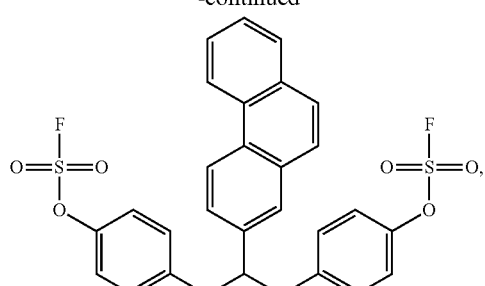
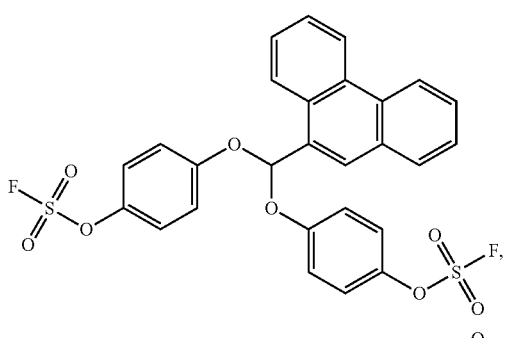
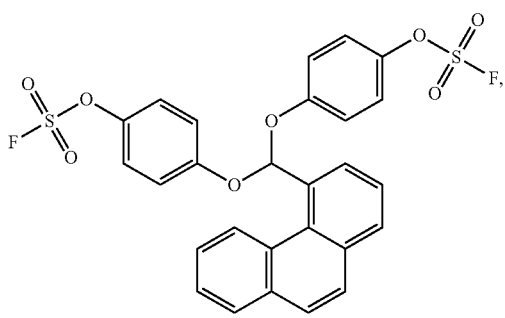
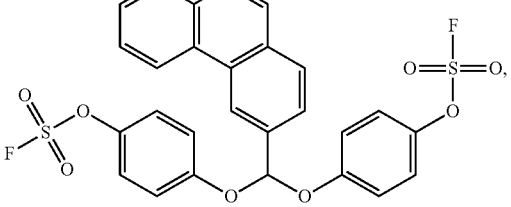
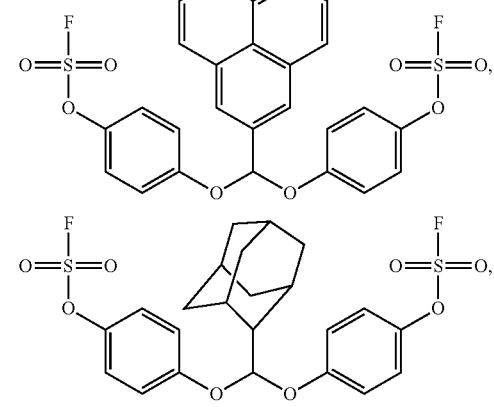

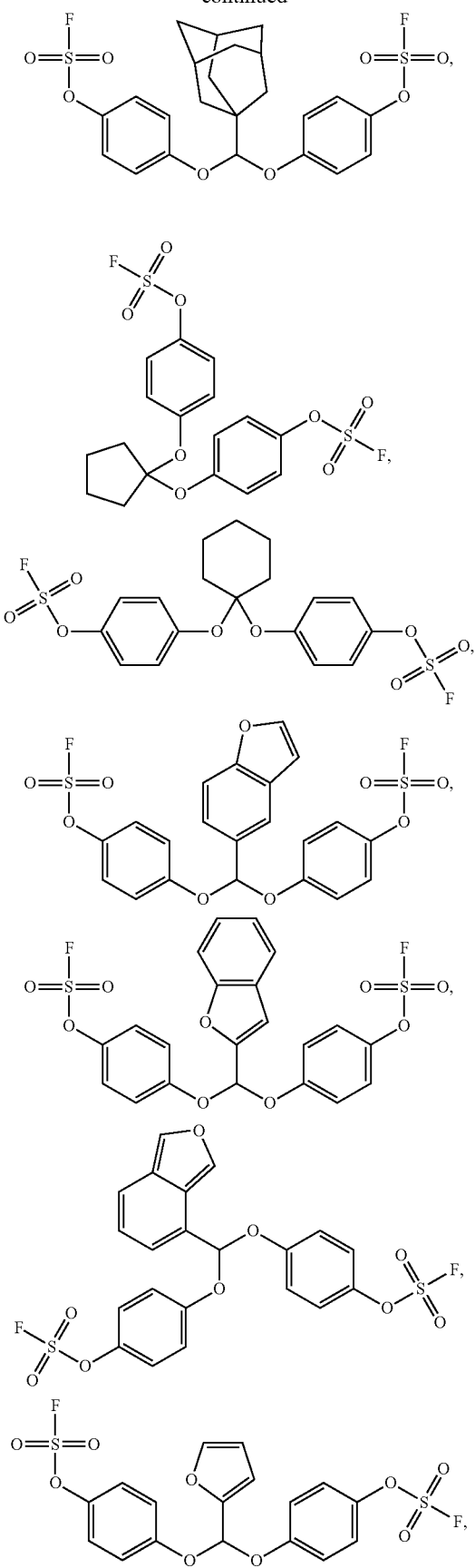
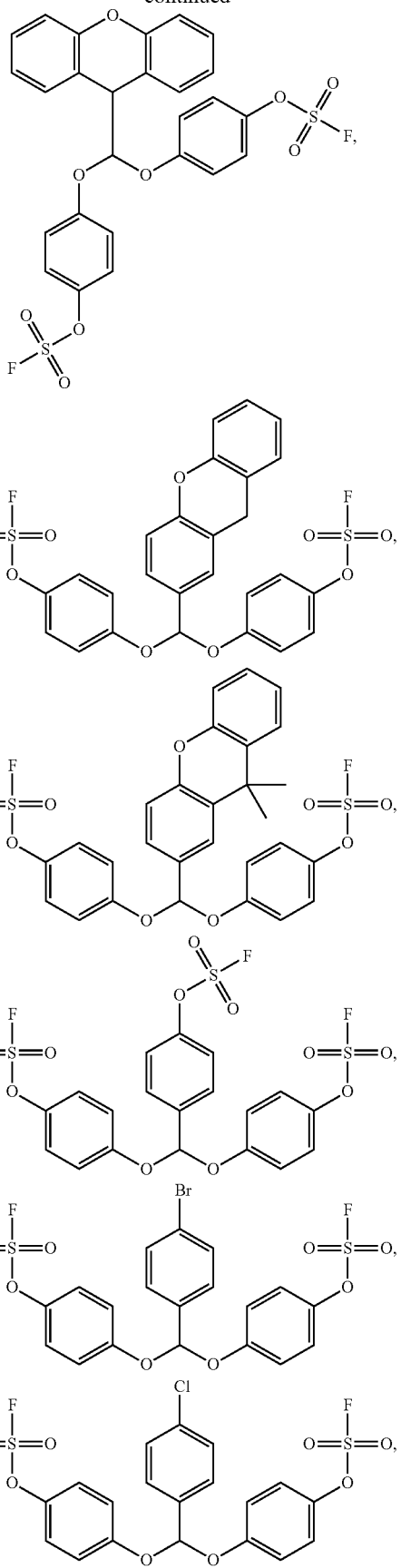

-continued
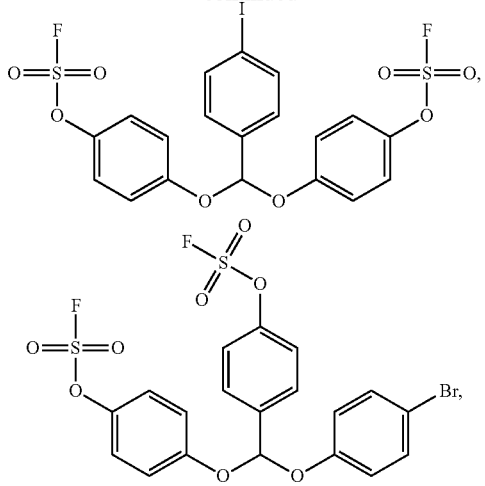
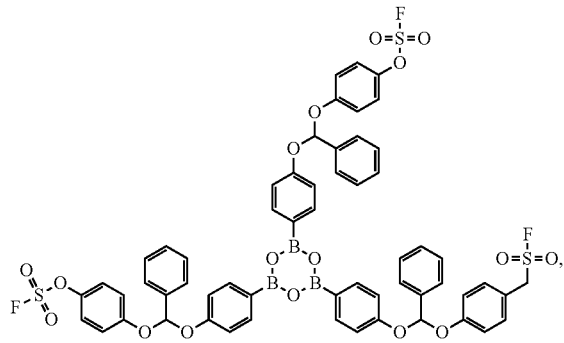
and combinations thereof.
* * * * *